United States Patent [19]

Sutter

[11] Patent Number: 5,451,595
[45] Date of Patent: Sep. 19, 1995

[54] NEMATICIDAL COMPOSITIONS

[75] Inventor: Marius Sutter, Binningen, Switzerland

[73] Assignee: Ciba-Geigy Corporation, Ardsley, N.Y.

[21] Appl. No.: 171,493

[22] Filed: Dec. 22, 1993

Related U.S. Application Data

[62] Division of Ser. No. 52,349, Apr. 23, 1993, abandoned, which is a division of Ser. No. 914,159, Jul. 14, 1992, abandoned.

[30] Foreign Application Priority Data

Jul. 17, 1991 [CH] Switzerland .......................... 2118/91

[51] Int. Cl.$^6$ ..................... C07D 275/04; A01N 43/80
[52] U.S. Cl. ...................................... 514/373; 548/207
[58] Field of Search ..................... 548/207; 514/373

[56] References Cited

U.S. PATENT DOCUMENTS

| | | | |
|---|---|---|---|
| 3,707,364 | 12/1972 | Becke et al. | 71/90 |
| 3,890,340 | 6/1975 | Singerman | 548/207 |
| 3,997,548 | 12/1976 | Singerman | 548/207 |
| 4,189,433 | 2/1980 | Ohnsorgi et al. | 548/207 |
| 4,589,910 | 5/1986 | Hagen | 71/90 |
| 5,169,951 | 12/1992 | Sutter et al. | 548/212 |

FOREIGN PATENT DOCUMENTS

| | | |
|---|---|---|
| 0039795 | 11/1981 | European Pat. Off. . |
| 0367365 | 5/1990 | European Pat. Off. . |
| 0454621 | 10/1991 | European Pat. Off. . |
| 2002891 | 10/1969 | France . |
| 1915387 | 10/1970 | Germany . |
| 2503699 | 8/1976 | Germany . |
| 2626967 | 12/1977 | Germany . |
| 3018108 | 11/1981 | Germany . |
| 1406882 | 9/1975 | United Kingdom . |

OTHER PUBLICATIONS

J. Chem. Soc. C pp. 3994–3999 (1971).
Jnn. Chim (Roma), 53, 577 (1963).
Jnn. Chim. (Roma), 53, pp. 1860–1868 (1963).
Meth—Cohn et al., Synthesis (i) pp. 58–60 (Jan. 1977).
L. K. A. Rahman et al., J. Chem. Soc., Perkin Trans. I, vol. 1983, pp. 2973–2977.
A. Franke et al., Irzneim-Forsch./ Drug Res., vol. 30 (II), pp. 1831–1838 (1980).
D. S. Kemp et al., Yetrokedron, vol. 21, pp. 3019–3035 (1965).

*Primary Examiner*—Robert Gerstl
*Attorney, Agent, or Firm*—Edward McC. Roberts

[57] ABSTRACT

Benzisothiazoles of the general formula I

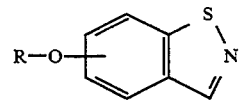

in which the group RO— is in one of the positions of the benzene ring and R is a pure or halogenated hydrocarbon radical which is aliphatic or cycloaliphatic, saturated or unsaturated, are active ingredients in crop protection products. They can be used for controlling nematodes which are parasites of plants.

6 Claims, No Drawings

NEMATICIDAL COMPOSITIONS

This application is a divisional of Ser. No. 08/052,349, filed Apr. 23, 1993, now abandoned, which is a divisional of Ser. No. 07/914,159, filed Jul. 14, 1992, now abandoned.

The present invention relates to novel nematicidal compositions which comprise, as active ingredient, at least one hydrocarbyloxybenzisothiazole of the general formula I, and to their use for controlling nematodes, in particular plant-injurious nematodes.

The invention furthermore relates to novel nematicidally active hydrocarbyloxybenzisothiazoles within the scope of the formula I and to processes for their preparation.

The benzisothiazoles of the present invention are those of the general formula I

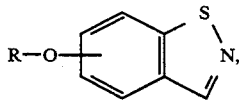

(I)

in which the group RO— is in one of the positions of the benzene ring and R is a pure or halogenated hydrocarbon radical which is aliphatic or cycloaliphatic, saturated or unsaturated.

The compounds known as nematicides have so far been unable to meet the demands encountered in practice.

It is therefore an aim of the present invention to provide novel nematicidal compositions which have advantageous properties.

By providing the compositions according to the invention which comprise, as active ingredient, the compounds of the formula I and additionally at least one carrier, it was possible for the applicant company to make a valuable contribution to the control of plant nematodes, which cause considerable agricultural damage to propagation stock. This allows yield reduction in crop plants to be reduced. Crops which may be mentioned in particular are potatoes, cereals, beet, oilseed rape, cabbage, tobacco, soybeans, cotton, maize, rice and vegetables, and plant material in tree nurseries and in the production of ornamentals. The compositions according to the invention are particularly distinguished by the effective control of soil nematodes which are root parasites, for example those of the genera Heterodera and Globodera (cyst nematodes), Meloidogyne (root knot nematodes) and those of the genera Radopholus, Pratylenchus, Tylenchulus, Longidorus, Trichodorus and Xiphinema. The compositions according to the invention also allow effective control of the nematode genera Ditylenchus (stem parasites), Aphelenchoides (folia nematodes) and Anguina (seed-gall nematodes).

Compositions which comprise, as active ingredient, the compounds of the formula I, are preferably suitable for the effective control of particularly harmful nematode species from the genus Meloidogyne, for example Meloidogyne incognita and from the genus Heterodera, for example Heterodera glycines (soybean cyst nematode).

To control the plant nematodes and to maintain healthy propagation stock, the novel active ingredients can be used curatively, preventively or systemically. They display a broad activity against the various nematode species and thus meet the requirements in practice.

EP-A-367 365 proposes, as nematicides, benzisothiazole derivatives of the formula

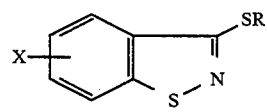

in which a halogenated hydrocarbon radical R which is bonded in the 3 position via a sulfur bridge is evidently the structural element which is essential for the action. This reference did not lead to any suggestion that the absence of this element would result in benzisothiazole derivatives whose nematicidal activity is far greater.

In fact, it is surprising that the phytotoxicity of the compounds of the formula I is nonexistent or only very low, but mainly that their acute toxicity to warm-blooded species is highly favourable and as little as one fiftieth of the toxicity of known nematicides from amongst the phosphates and carbamates. With these two properties, the present active ingredients of the formula I outperform the large number of preparations which have previously been proposed as plant nematicides.

The present invention therefore is an entirely uncommon enrichment of the art.

Unless otherwise defined, the general terms used hereinbefore and hereinafter have the meanings mentioned below:

halogen is fluorine, chlorine, bromine or iodine, mainly fluorine, chlorine or bromine, in particular fluorine.

Hydrocarbon radicals can have 1 to 4 C atoms, preferably 1–3 C atoms, and, depending on the number of the C atoms, can be straight-chain such as methyl, ethyl, propyl or butyl, or branched such as isopropyl, isobutyl, sec-butyl or tert-butyl.

Examples of cycloaliphatic hydrocarbon radicals are cyclopropyl, methylcyclopropyl, cyclopropylmethyl or cyclobutyl.

Unsaturated hydrocarbon radicals have at least one double bond and/or one triple bond and, depending on the number of the C atoms, can be straight-chain, such as vinyl, allyl, butenyl, propynyl or butynyl, or branched, such as methylallyl.

Halogenated hydrocarbon radicals can be saturated or unsaturated, aliphatic or cycloaliphatic and partially halogenated or perhalogenated. Examples are fluoromethyl, difluoromethyl, trifluoromethyl, 1,2-difluoroethyl, difluorobutenyl, chloroallyl, dichlorovinyl, bromovinyl, bromopropynyl and 1-fluorocyclopropyl.

The substituent RO— can be in each of the four positions 4, 5, 6 or 7 of the benzene moiety in the molecule. One of the preferred positions is the 7 position adjacent to the S atom.

7-Methoxybenzisothiazole is known from J. Chem. Soc. Perkin Trans I (1983), pages 2973–2977. No technical use was described in this publication.

4-Methoxybenzisothiazole was described in J. Chem. Soc. C)3994–3999 (1971)without a technical use being mentioned.

Preferred compositions within the scope of this invention are those in which the active component is a compound of the formula I in which R is a halogenated or unhalogenated hydrocarbon radical having not more than 4 C atoms.

Particularly preferred compositions are those which comprise, as active component, a compound of the formula I'

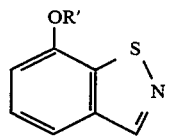

in which R' is a halogenated or unhalogenated hydrocarbon having 1 to 3 C atoms.

A further preferred group of compositions comprises, as active component, a compound selected from amongst 7-methoxybenzisothiazole, 7-difluoromethoxybenzisothiazole, 7-allyloxybenzisothiazole, 7-propargyloxybenzisothiazole, 4-methoxybenzisothiazole, 5-methoxybenzisothiazole and 6-methoxybenzisothiazole.

Other preferred compositions comprise, as active component, 6-ethoxybenzisothiazole and 6-allyloxybenzisothiazole.

A very particularly preferred composition comprises, as active component, 7-methoxybenzisothiazole.

The present invention furthermore relates to hydrocarbyloxybenzisothiazoles of the formula I''

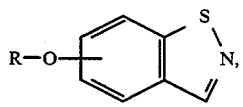

in which the group RO— is in one of the positions of the benzene ring and R is a pure or halogenated hydrocarbon radical which is aliphatic or cycloaliphatic and saturated or unsaturated, with the proviso that a methoxy group in the 4- or 7-position is halogenated. 6-Ethoxybenzisothiazole and 6-allyloxybenzisothiazole are preferred.

The invention furthermore relates to a process for the preparation of the compounds of the formula I which comprises reacting a substituted halobenzaldehyde of the formula II with a thiol $R_8SH$ in solution and in the presence of a base to give the thioether of the formula III, and reacting the latter, with or without isolation, with hydroxylamine-O-sulfonic acid in solution, and cyclising the product to give the desired compound,

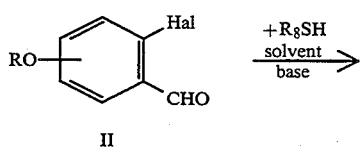

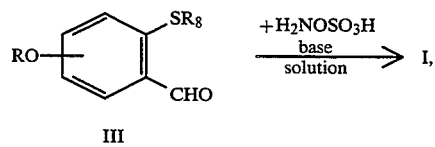

in which Hal is halogen and $R_8$ is $C_1$-$C_{30}$alkyl, $C_3$-$C_7$cycloalkyl or benzyl.

Examples of suitable bases for the first step of this reaction sequence are hydrides, amides, alcoholates, carbonates or hydrogen carbonates of alkali metals or alkaline earth metals, preferably potassium carbonate or sodium carbonate. It is advantageous to carry out the reaction in alcohols or in aprotic solvents, for example dimethylformamide, dimethyl sulfoxide, dimethylpropyleneurea or dimethylethyleneurea, or in ethers such as diethyl ether or tetrahydrofuran, at 0°–70° C., preferably at room temperature. The reaction can also be carded out in the presence of metal salts, for example copper, nickel or palladium salts.

Suitable bases for the second step are alkali metal carbonates or alkali metal hydrogen carbonates, for example sodium hydrogen carbonate; furthermore tert-amines, for example triethylamine or pyridine. Suitable substances for the second step are aprotic organic solvents, for example methylene chloride; ethers, for example diethyl ether, dioxane or tetrahydrofuran; esters, for example ethyl acetate, hydrocarbons, for example hexane, cyclohexane, methylcyclohexane or toluene, and their mixtures with water. The reaction temperature of the second step is between —20° and 100° C., preferably 20° to 50° C.

A preferred embodiment of the process comprises reacting the thioether of the formula III with hydroxylamine-O-sulfonic acid in solution and cyclising by addition of a base to give the desired product.

A further embodiment for the preparation of compounds of the formula Ib

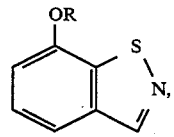

comprises reacting a benzaldehyde of the formula IV with benzylmercaptan in solution, reacting the product in the presence of a base to give the thioether of the formula V, reacting the latter, with or without isolation, with hydroxylamine-O-sulfonic acid in solution, and cyclising the product to give the desired compound,

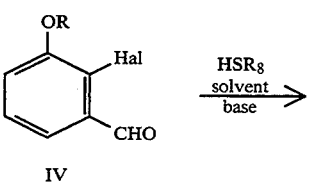

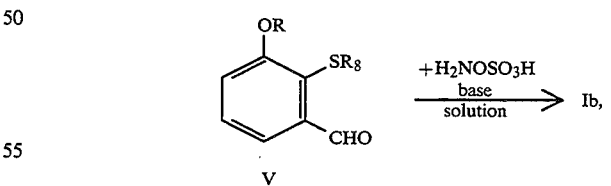

in which Hal is halogen and $R_8$ is benzyl.

A preferred embodiment comprises reacting the thioether of the formula V with hydroxylamine-O-sulfonic acid in solution and cyclising to give the desired product; it is especially preferred to react the intermediate of the formula V with hydroxylamine-O-sulfonic acid at pH=4—6 and to carry out the cyclisation by subsequently adding a base.

A further embodiment for the preparation of compounds of the formula I comprises reacting a benzaldehyde derivative of the formula VI with hydroxylamine or with a salt thereof to give the corresponding oxime of the formula VII and cyclising the latter with a strong water-binding acid, R being as defined in formula I and $R_8$ being $C_1$-$C_{30}$alkyl, $C_3$-$C_7$cycloalkyl or benzyl.

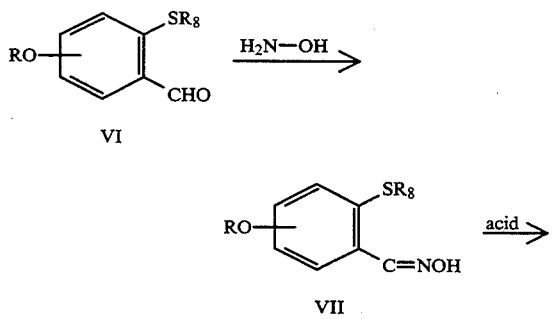

In the cyclisation, polyphosphoric acid or phosphorus pentoxide in methanesulfonic acid is preferably used as strong acid; the reaction is especially preferably carried out in a mixture of 1-20 per cent by weight of phosphorus pentoxide in methanesulfonic acid at $\Delta 10°$ to 100° C.

Compounds of the formula I can furthermore be prepared by reacting a phenol-type hydroxybenzisothiazole of the formula VIII

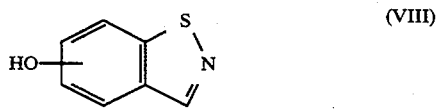

with a reagent R-X in which R is as defined in formula I and X is halogen, tosylate or mesylate.

The novel intermediates of the formula III which were hitherto unknown are a further object of the present invention.

Intermediates from amongst the compounds of the formula III which must be emphasised in connection with synthesis are those in which $R_8$ is $C_1$—$C_6$alkyl or the benzyl radical.

The starting materials for the preparation processes mentioned are either known, commercially available compounds, or they can be prepared by known processes.

The novel intermediates of the formula VIII which were hitherto unknown, namely 6-hydroxybenzisothiazole and 7-hydroxybenzisothiazole, are a further object of the present invention.

In principle, they can be prepared by the methods described above.

In addition, the present invention includes the preparation of nematicidal compositions, which comprises intimately mixing active ingredients of the formula I with one or more carriers and adjuvants described herein. Accordingly, the compositions according to the invention comprise an effective amount of at least one of the compounds of the formula I.

The invention also embraces a method of treating plants by applying a compound of the formula I or a composition comprising at least one compound of the formula I to the plant, to pans of the plant, or to the culture substrate of the plant. Preferred compounds are 7-methoxybenzisothiazole, 7-difluoromethoxybenzisothiazole, 7-allyloxybenzisothiazole, 7-propargyloxybenzisothiazole, 4-methoxybenzisothiazole, 5-methoxybenzisothiazole, 6-methoxybenzisothiazole; 7-methoxybenzisothiazole is particularly preferred. Other preferred compounds are 6-ethoxybenzisothiazole and 6-allyloxybenzisothiazole.

Alternatively, the compounds of the formula I can be applied to seeds (coating), either by allowing the kernels to absorb a liquid preparation of the active ingredient or by applying a coating of a solid preparation to the kernels. Moreover, other types of application are possible in specific cases, for example the targeted treatment of the stalks of the plants, or of the buds or leaves.

The compounds of the formula I are used in unaltered form or, preferably, together with the adjuvants customary in the art of formulation. They are processed in a known manner to give, for example, emulsion concentrates, directly sprayable or dilutable solutions, dilute emulsions, wettable powders, soluble powders, dusts, granules, by encapsulations, for example in polymeric substances. The application methods such as spraying, dusting, scattering or pouring, and the nature of the compositions are selected to suit the intended aims and the prevailing circumstances. Expedient rates of application are generally 0.1 to 10 kg of active ingredient (a.i.) per ha; preferably 0.3 to 5 kg of a.i./ha. When used for seed dressing, the active ingredients are advantageously used at dosage rates from 0.001 to 2 g of a.i. per kg of seed.

Active ingredients of the formula I are customarily used in the form of formulated compositions and can be applied to the area or plant treated together with other active ingredients, either simultaneously or in succession. These other active ingredients can also embrace other compositions used in agriculture whose application is intended to increase production by enhancing the growth of the useful plants, such as inter alia fertilisers, herbicides, insecticides, fungicides, molluscicides, or mixtures of more than one of these preparations, if appropriate together with other solvents, carders, surfactants or other application-enhancing additives customary in the art of formulation.

Suitable carders and additives can be solid or liquid and are substances expedient in the art of formulation, for example natural or regenerated mineral substances, solvents, dispersants, wetting agents, adhesives, thickeners, binders or fertilisers.

The following are suitable as solvents: aromatic hydrocarbons, preferably the fractions $C_8$ to $C_{12}$, for example xylene mixtures or substituted naphthalenes, phthalic esters such as dibutyl phthalate or dioctyl phthalate, aliphatic hydrocarbons such as cyclohexane or paraffins, alcohols and glycols as well as their ethers and esters, such as ethanol, ethylene glycol, ethylene glycol monomethyl ether or -ethyl ether, ketones such as cyclohexanone, strongly polar solvents such as N-methyl-2-pyrrolidone, dimethyl sulfoxide or dimethylformamide, and epoxidised and unepoxidised vegetable oils such as epoxidised coconut oil or soya oil; or water.

Solid carriers which are generally used, for example for dusts and dispersible powders, are natural ground minerals such as calcite, talc, kaolin, montmorillonite or attapulgite. To improve the physical properties, it is also possible to add highly disperse silica or highly disperse absorptive polymers. Suitable particulate, adsorptive carriers for granules are porous types, for example pumice, brick grit, sepiolite or bentonire, suitable non-sorptive carrier materials are, for example, calcite or sand. Moreover, a large number of preganulated materials of inorganic or organic nature can be used, such as, in particular, dolomite or comminuted plant residues.

Suitable surface-active substances are, depending on the nature of the active ingredient of the formula I to be formulated, non-ionic, cationic and/or anionic surfactants which have good emulsifying, dispersing and wetting properties. Surfactants are also to be understood as meaning surfactant mixtures.

Suitable anionic surfactants can be so-called water-soluble soaps as well as water-soluble synthetic surface-active compounds.

Soaps which may be mentioned are the alkali metal salts, alkaline earth metal salts or substituted or unsubstituted ammonium salts of higher fatty acids ($C_{10}$-$C_{22}$), for example the sodium or potassium salts of oleic or stearic acid, or of natural fatty acid mixtures which can be obtained, for example, from coconut oil or tallow oil. Other substances which may be mentioned are the fatty acid methyl laurinates and modified and unmodified phospholipids.

However, so-called synthetic surfactants are used more frequently, in particular fatty sulfonates, fatty sulfates, sulfonated benzimidazole derivatives or alkylarylsulfonates.

Other suitable substances are corresponding phosphates, for example salts of the phosphoric ester of a p-nonylphenol-(4-14) ethylene oxide adduct.

Suitable nonionic surfactants are mainly polyglycol ether derivatives of aliphatic or cycloaliphatic alcohols, saturated or unsaturated fatty acids and alkylphenols which can contain 3 to 30 glycol ether groups and 8 to 20 carbon atoms in the (aliphatic) hydrocarbon radical and 6 to 18 carbon atoms in the alkyl radical of the alkylphenols.

Other suitable nonionic surfactants are the water-soluble polyethylene oxide adducts with polypropylene glycol, ethylenediaminopolypropylene glycol and alkylpolypropylene glycol having 1 to 10 carbon atoms in the alkyl chain and which contain 20 to 250 ethylene glycol ether groups and 10 to 100 propylene glycol ether groups. The compounds mentioned usually contain 1 to 5 ethylene glycol units per propylene glycol unit.

Examples of nonionic surfactants which may be mentioned are nonylphenolpolyethoxyethanols, castor oil polyglycol ether, polypropylene/polyethylene oxide adducts, tributylphenoxypolyethoxyethanol, polyethylene glycol and octylphenoxypol yethoxye thanol.

Other suitable substances are fatty acid esters of polyoxyethylene sorbitan, such as polyoxyethylene sorbitan trioleate.

The cationic surfactants are mainly quaternary ammonium salts which contain, as N-substituents, at least one alkyl radical having 8 to 22 C atoms, and as further substituents lower halogenated or nonhalogenated alkyl radicals, benzyl radicals or lower hydroxyalkyl radicals. The salts are preferably in the form of halides, methylsulfates or ethylsulfates, for example stearyltrimethylammonium chloride or benzyldi(2-chloroethyl)ethylammonium bromide.

The novel surfactants customary in the art of formulation are described, inter alia, in the following publications:

"Mc Cutcheon's Detergents and Emulsifiers Annual" MC Publishing Corp., Ridgewood, N.J., 1979; Dr. Helmut Stache "Tensid Taschenbuch [Surfactants Guide]", Carl Hanser Verlag Munich/Vienna.

The agrochemical preparations comprise an effective amount, i.e., as a rule, 0.1 to 99% by weight, in particular 0.1 to 95% by weight, of active ingredient of the formula I, 99.9 to 1% by weight, in particular 99.8 to 5% by weight, of a solid or liquid additive, and 0 to 25% by weight, in particular 0.1 to 25% by weight, of a surfactant.

While concentrated compositions are more preferred as commercially available goods, the end user will use, as a rule, dilute compositions.

The compositions can also comprise further additives such as stabilisers, defoamers, viscosity regulators, binders, adhesives as well as fertilisers or other active ingredients for achieving specific effects.

The examples which follow are intended to illustrate the invention in greater detail without restricting it.

H. Preparation Examples:

H.1 Preparation of 7-methoxybenzisothiazole [Process 1][Comp. No. 1.1]

136.5 g of 2-chloro-3-methoxybenzaldehyde and 136.5 g of potassium carbonate are stirred in 800 ml of dimethylformamide. 90.6 ml of benzylmercaptan are added dropwise to the suspension, and the mixture is stirred overnight at room temperature and then for one day at 100° C. The reaction mixture is poured into water and extracted using diethyl ether. The organic phase is dried over sodium sulfate, filtered and concentrated. The resulting oil is introduced into 500 ml of water (buffered to a pH of 5), and 110.7 g of hydroxylamine-O-sulfonic acid are added to the mixture, with ice-cooling. After the mixture has been stirred for 1 hour at room temperature, 300 ml of water and 300 ml of methylene chloride are added, and the batch is treated with 276.6 g of sodium hydrogen carbonate, in portions. The reaction mixture is stirred for 2 hours at room temperature and then extracted using methylene chloride, and the organic phase is washed with concentrated NaCl solution (saline), dried over sodium sulfate, filtered and concentrated.

7-Methoxybenzisothiazole, $n_D^{20}$=1.6190, is obtained from the resulting oil after purification by chromatography.

H.2 Preparation of 7-methoxybenzisothiazole [Process 2]

5 g of 2-benzylthio-3-methoxybenzaldehyde are dissolved in 40 ml of ethanol, and 3.9 g of hydroxylamine hydrochloride are added. 40 ml of acetate buffer (pH=5) are added to this solution, and the mixture is stirred for 30 minutes at room temperature. The mixture is poured into water and extracted using ethyl acetate. The organic phase is washed using saline, dried over sodium sulfate, filtered and concentrated. The resulting oil is added to a suspension of 1.6 g of phosphorus pentoxide in20 ml of methanesulfonic acid, and the mixture is stirred overnight at room temperature. The reaction mixture is poured onto ice and extracted using ethyl acetate. The organic phase is washed with saturated sodium hydrogen carbonate solution and with saline and dried over sodium sulfate, filtered and concentrated. After purification by chromatography, 7-methoxybenzisothiazole is obtained in the form of an oil.

H.3 Preparation of 7-hydroxybenzisothiazole (intermediate)

174 g of 2-chloro-3-hydroxybenzaldehyde are dissolved in 1 l of dimethylformamide, 126 ml of benzylmercaptan and 174 g of potassium carbonate are added, and the mixture is stirred for 2 days at 100° C. The reaction mixture is poured into ice-water and extracted using diethyl ether, and the organic phase is washed with saline, dried over sodium sulfate, filtered and concentrated. Silica gel chromatography with ethyl acetate/hexane (1:4) as the mobile phase gives 51.6 g of 2-benzylthio-3-hydroxybenzaldehyde. 31.6 g of this are emulsified in 66 ml of water, and 16.1 g of hydroxylamine-O-sulfonic acid and 1.84 g of sodium sulfate are added. After one hour, 32 ml of each water and methylene chloride are added, and the mixture is treated with 40.4 g of sodium hydrogen carbonate in portions. The reaction mixture is stirred for 2 hours at room temperature and then taken up in methylene chloride, and the organic phase is extracted using 1N potassium hydroxide solution. The aqueous-basic phase is brought to a pH of 1 using concentrated hydrochloric acid and extracted using methylene chloride. The organic phase is dried over sodium sulfate, filtered and concentrated. Recrystallisation from toluene gives 5.93 g of 7-hydroxy-1,2-benzisothiazole of m.p. 185°–187° C.

H.4 Preparation of 7-allyloxybenzisothiazole [Compound No. 1.9]

2.0 g of 7-hydroxy-1,2-benzisothiazole are dissolved in 20 ml of THF, and 460 mg of sodium hydride (60%) are added to the mixture at 0° C. When the evolution of gas has ended, 1 ml of allyl bromide is added dropwise, the reaction mixture is stirred for one day at room temperature. Again, 1 ml of allyl bromide and 40 mg of sodium hydride are added, and the mixture is stirred for 2 days under reflux. The reaction mixture is poured into water, rendered basic using 1 N potassium hydroxide solution and extracted using ethyl acetate. The organic phase is washed with saline, dried over sodium sulfate, filtered and concentrated. Silica gel chromatography with ethyl acetate/hexane (1:5) as mobile phase gives 2.0 g of 7-allyloxy-1,2-benzisothiazole; $n_D^{20} = 1.6039$.

H.5 Preparation of 7-difluoromethoxy-1,2-benzisothiazole [Comp. No. 1.2]

2.0 g of 7-hydroxy-1,2-benzisothiazole are dissolved in 40 ml of acetonitrile, and 10.8 g of solid potassium carbonate are added. Freon 22 is passed in at 70° C. in the course of 18 hours. When gas is no longer passed in, the mixture is filtered and the flitrate is concentrated. Silica gel chromatography with ethyl acetate/hexane (4:1) as mobile phase yields 370 mg of 7-difluoromethoxy-1,2-benzisothiazole; m.p. 58–59° C.

The following 7-substituted benzisothiazoles can be prepared analogously:

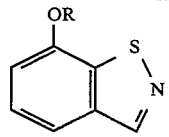

| Comp. No. | R | Physical data |
|---|---|---|
| 1.1 | —CH₃ | $n_D^{20} = 1.6190$ |
| 1.2 | —CHF₂ | m.p. 58–59° C. |
| 1.3 | —CH₂F | |
| 1.4 | —C₂H₅ | $n_D^{20} = 1.5923$ |
| 1.5 | —CHF—CH₂F | |
| 1.6 | —CH=CH₂ | |
| 1.7 | —CH₂—C≡CH | m.p. 74–76° C. |
| 1.8 | —CH₂—C≡CBr | |
| 1.9 | —CH₂—CH=CH₂ | $n_D^{20} = 1.6039$ |
| 1.10 | —CH₂—C(CH₃)=CH₂ | |
| 1.11 | cyclopropyl | |
| 1.12 | 1-fluorocyclopropyl | |
| 1.13 | —C≡CH | |
| 1.14 | isopropyl | $n_D^{20} = 1.5680$ |
| 1.15 | tert-butyl | $n_D^{20} = 1.5669$ |
| 1.16 | —CF₃ | $R_f = 0.60$ [hexane/ethyl acetate 1:1] |
| 1.17 | —CH=CHBr | $n_D^{20} = 1.3005$ |
| 1.18 | —CH₂CH₂CF=CF₂ | $n_D^{20} = 1.5025$ |
| 1.19 | —CH₂CH₂CH₃ | $n_D^{20} = 1.5815$ |
| 1.20 | cyclopropylmethyl | $n_D^{20} = 1.5902$ |
| 1.21 | —CH=CCl₂ | m.p. 73–74° C. |

The following 4-substituted benzisothiazoles can be prepared analogously:

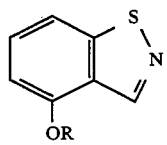

| Comp. No. | R | Physical data |
|---|---|---|
| 2.1 | —CH₃ | m.p. 70–71° C. |
| 2.2 | —CHF₂ | |
| 2.3 | —CH₂F | |
| 2.4 | —C₂H₅ | |
| 2.5 | —CHF—CH₂F | |
| 2.6 | —CH=CH₂ | |
| 2.7 | —CH₂—C≡CH | |
| 2.8 | —CH₂—C≡CBr | |
| 2.9 | —CH₂—CH=CH₂ | |
| 2.10 | —CH₂—C(CH₃)=CH₂ | |
| 2.11 | cyclopropyl | |
| 2.12 | 1-fluorocyclopropyl | |
| 2.13 | —C≡CH | |
| 2.14 | isopropyl | |
| 2.15 | tert-butyl | |
| 2.16 | —CF₃ | |

The following 5-substituted benzisothiazoles can be prepared analogously:

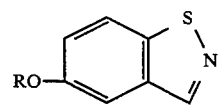

| Comp. No. | R | Physical data |
|---|---|---|
| 3.1 | —CH₃ | $n_D^{20} = 1.6021$ |
| 3.2 | —CHF₂ | |
| 3.3 | —CH₂F | |
| 3.4 | —C₂H₅ | |

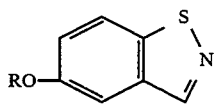

| Comp. No. | R | Physical data |
|---|---|---|
| 3.5 | —CHF—CH$_2$F | |
| 3.6 | —CH=CH$_2$ | |
| 3.7 | —CH$_2$—C≡CH | |
| 3.8 | —CH$_2$—C≡CBr | |
| 3.9 | —CH$_2$—CH=CH$_2$ | |
| 3.10 | —CH$_2$—C(CH$_3$)=CH$_2$ | |
| 3.11 | cyclopropyl | |
| 3.12 | 1-fluorocyclopropyl | |
| 3.13 | —C≡CH | |
| 3.14 | isopropyl | |
| 3.15 | tert-butyl | |
| 3.16 | —CF$_3$ | |

The following 6-substituted benzisothiazoles can be prepared analogously:

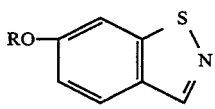

| Comp. No. | R | Physical data |
|---|---|---|
| 4.1 | —CH$_3$ | $n_D^{20}$ = 1.6235 |
| 4.2 | —CHF$_2$ | |
| 4.3 | —CH$_2$F | |
| 4.4 | —C$_2$H$_5$ | m.p. 48–50° C. |
| 4.5 | —CHF—CH$_2$F | |
| 4.6 | —CH=CH$_2$ | |
| 4.7 | —CH$_2$—C≡CH | |
| 4.8 | —CH$_2$—C≡CBr | |
| 4.9 | —CH$_2$—CH=CH$_2$ | $n_D^{20}$ = 1.6093 |
| 4.10 | —CH$_2$—C(CH$_3$)=CH$_2$ | |
| 4.11 | cyclopropyl | |
| 4.12 | 1-fluorocyclopropyl | |
| 4.13 | —C≡CH | |
| 4.14 | isopropyl | |
| 4.15 | tert-butyl | |
| 4.16 | —CF$_3$ | |

F. Formulation examples of liquid active ingredients of the formula I (%=per cent by weight)

| F.1 Emulsion concentrates | a) | b) | c) |
|---|---|---|---|
| Active ingredient of Tables 1–4 | 25% | 40% | 50% |
| Calcium dodecylbenzenesulfonate | 5% | 8% | 6% |
| Castor oil polyethylene glycol ether (36 mol of ethylene oxide) | 5% | — | — |
| Tributylphenol polyethylene glycol ether (30 mol of ethylene oxide) | — | — | 12% |
| Cyclohexanone | — | 15% | 20% |
| Xylene mixture | 65% | 25% | 20% |

Emulsions of any desired concentration can be prepared from such concentrates by dilution with water.

| F.2 Solutions | a) | b) | c) | d) |
|---|---|---|---|---|
| Active ingredient of Tables 1–4 | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidised coconut oil | — | — | 1% | 5% |
| Petroleum spirit (boiling range 160–190° C.) | — | — | 94% | — |

(MW = molecular weight)

The solutions are suitable for use in the form of very small drops.

| F.3 Granules | a) | b) |
|---|---|---|
| Active ingredient of Tables 1–4 | 5% | 10% |
| Kaolin | 94% | — |
| Highly disperse silica | 1% | — |
| Attapulgite | — | 90% |

The active ingredient is dissolved in methylene chloride, sprayed onto the carrier, and the solvent is subsequently removed by evaporation in vacuo.

| F.4 Dusts | a) | b) |
|---|---|---|
| Active ingredient of Tables 1–4 | 2% | 5% |
| Highly disperse silica | 1% | 5% |
| Talc | 97% | — |
| Kaolin | — | 90% |

Ready-to-use dusts are obtained by intimately mixing the carders with the active ingredient.

| F.5 Wettable powders | a) | b) | c) |
|---|---|---|---|
| Active ingredigent of Tables 1–4 | 25% | 50% | 75% |
| Sodium ligninsulfonate | 5% | 5% | — |
| Sodium lauryl sulfate | 3% | — | 5% |
| Sodium diisobutylnaphthalenesulfonate | — | 6% | 10% |
| Octylphenol polyethylene glycol ether (7–8 mol of ethylene oxide) | — | 2% | — |
| Highly disperse silica | 5% | 10% | 10% |
| Kaolin | 62% | 27% | — |

The active ingredient is mixed thoroughly with the additives, the mixture is ground thoroughly in a suitable mill. This gives wettable powders which can be diluted with water to give suspensions of any desired concentration.

| F.6 Emulsion concentrate | |
|---|---|
| Active ingredient of Tables 1–4 | 10% |
| Octylphenol polyethylene glycol ether (4–5 mol of ethylene oxide) | 3% |
| Calcium dodecylbenzenesulfonate | 3% |
| Castor oil polyglycol ether (35 mol of ethylene oxide) | 4% |
| Cyclohexanone | 30% |
| Xylene mixture | 50% |

Emulsions of any desired concentration can be prepared from this concentrate by dilution with water.

| F.7 Dusts | a) | b) |
|---|---|---|
| Active ingredient of Tables 1–4 | 5% | 8% |
| Talc | 95% | — |
| Kaolin | — | 92% |

Ready-to-use dusts are obtained by mixing the active ingredient with the carders and grinding the mixture on a suitable mill.

| F.8 Extruder granules | |
|---|---|
| Active ingredient of Tables 1-4 | 10% |
| Sodium ligninsulfonate | 2% |
| Carboxymethylcellulose | 1% |
| Kaolin | 87% |

The active ingredient is mixed with the additives, and the mixture is ground and moistened with water. This mixture is extruded and subsequently dried in a stream of air.

| F.9 Coated granules | |
|---|---|
| Active ingredient of Tables 1-4 | 3% |
| Polyethylene glycol (MW 200) | 3% |
| Kaolin | 94% |

(MW = molecular weight)

In a mixer, the kaolin which has been moistened with polyethylene glycol is coated uniformly with the finely ground active ingredient. Dust-free coated granules are obtained in this manner.

B. Biological examples

B.1 Action against Meloidogyne incognita on tomatoes

Eggs of Meloidogyne incognita are mixed with sand. This mixture is then used for filling clay pots having a volume of 200 ml (5000 eggs per pot). The same day, one 3-week-old tomato plant is planted per pot, and the formulated active ingredient is introduced into the pots by means of drench application (0.0006% of active ingredient relative to the soil volume). The potted plants are now placed in a greenhouse at a temperature of 26+1 ° C. and a relative atmospheric humidity of 60%. After 4 weeks have elapsed, the plants are evaluated by assessing the formation of root knots using the so-called root knot index.

Untreated but infected control plants display severe formation of root knots (=100%). In contrast, the compounds of the formula I show a good action, the residual infestation being less than 20%. Compounds Nos. 1.1, 1.2, 1.9, 2.1, 3.1, 4.1, 4.4, 4.9 and others even show virtually complete inhibition of root knot formation in the above test (0-10% residual infestation).

B.2 Action against Heterodera glycines on soybeans

Sandy soil is infested with eggs of the soybean cyst nematode H. glycines, approx. 6000 eggs per pot. Suitable concentrations of the test substances are then incorporated by mixing. The treated and infested soil is then used for filling lc pots (180 ccm ), and three soybeans (cv. Maple Arrow) are placed into each pot. Each treatment has three replications. The pots are incubated in the greenhouse for four to five weeks at approx. 27° C. The plants are then carefully removed from the pots, the roots are washed, and the number of cysts is determined.

The compounds of Tables 1-4 show a good action against Heterodera glycines, which is shown by the fact that cyst formation is virtually completely reduced. Compounds 2.1, 3.1, 4.1, 4.4 and 4.9 must be mentioned in particular.

What is claimed is:

1. A composition for controlling or preventing attack of plants by nematodes, which comprises, besides an inert carrier material, at least one compound of the formula I

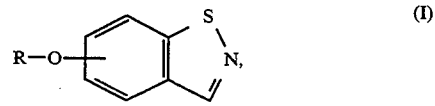

in which the group RO— is in one of the positions of the benzene ring and R is unhalogenated or halogenated hydrocarbon radical having not more than 4 C atoms which is aliphatic or cycloaliphatic and saturated or unsaturated.

2. A composition according to claim 1, which comprises, as active component, a compound of the formula I'

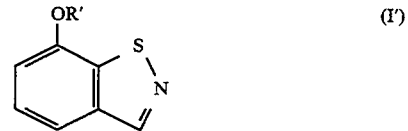

in which R' is a halogenated or unhalogenated hydrocarbon radical having 1 to 3 C atoms.

3. A composition according to claim 1, which comprises, as active component, a compound selected from 6-ethoxybenzisothiazole and 6-allyloxybenzisothiazole.

4. A composition according to claim 1, which comprises, as active component, 7-methoxybenzisothiazole.

5. A method for controlling or preventing attack of crop plants by nematodes, which comprises applying a compound of the formula I or a composition comprising at least one compound of the formula I to the plant, to parts of the plant or to the locus of the plants.

6. 6-Ethoxybenzisothiazole or 6-allyloxybenzisothiazole.

* * * * *